United States Patent [19]

Reddy

[11] Patent Number: 5,352,219
[45] Date of Patent: Oct. 4, 1994

[54] MODULAR TOOLS FOR LAPAROSCOPIC SURGERY

[76] Inventor: Pratap K. Reddy, 5610 Hyland Greens Dr., Bloomington, Minn. 55437

[21] Appl. No.: 953,865

[22] Filed: Sep. 30, 1992

[51] Int. Cl.$^5$ .............................................. A61B 17/00
[52] U.S. Cl. ........................................ 606/1; 606/190; 606/113; 606/114; 606/127; 606/185
[58] Field of Search .................. 606/205, 207, 1, 190, 606/113, 114, 148, 127, 185

[56] References Cited

U.S. PATENT DOCUMENTS

| | | | |
|---|---|---|---|
| 2,117,312 | 5/1938 | Gauly | 606/1 |
| 2,143,910 | 1/1939 | Didusch | |
| 5,006,106 | 4/1991 | Angelchik | 600/37 |
| 5,015,250 | 5/1991 | Foster | 606/147 |
| 5,053,043 | 10/1991 | Gottesman et al. | 606/148 |
| 5,084,005 | 1/1992 | Kachigian | 604/1 |
| 5,171,240 | 12/1992 | Hanwong | 606/1 |

FOREIGN PATENT DOCUMENTS

| | | | |
|---|---|---|---|
| 668675 | 7/1979 | U.S.S.R. | 606/207 |
| 1537229 | 1/1990 | U.S.S.R. | 606/127 |

OTHER PUBLICATIONS

W. Schuessler and T. G. Vancaillie, Techniques in Endosurgery, Laparoscopic Lymphadenectomy, Ethicon publication No. END035.

*Primary Examiner*—Tamara L. Graysay
*Attorney, Agent, or Firm*—Moore & Hansen

[57] ABSTRACT

A two-part modular tool and method for use thereof in conjunction with laparoscopic techniques enhances such techniques by enabling tools to be manipulated within a body cavity through small needle holes. The tool has an instrument head initially inserted through a laparoscopic port and an acuminate shaft which intracorporeally attaches to the instrument head. The instrument head is then manipulable through the needle hole at the site of desired use. The instrument head may be any tool configuration useful in surgical procedures which can be miniaturized to pass through a laparoscopic port.

23 Claims, 4 Drawing Sheets

MODULAR TOOLS FOR LAPAROSCOPIC SURGERY

BACKGROUND OF THE INVENTION

This invention relates generally to tools and methods for surgical procedures. More specifically, this invention pertains to tools and methods useful in conjunction with laparoscopic surgery procedures.

In laparoscopic surgery, a trocar, or more typically, a series of trocars is mounted through the wall of the body cavity in which surgery is to be performed. These trocars provide spaced ports into the cavity for insertion and manipulation of special narrow surgical instruments. Insufflation of the body cavity may be carded out and maintained by seals on the trocar port which permit tool manipulation without excessive loss of insufflation gas. A video camera is generally operated through a trocar port for visualization and control of the procedures in the cavity.

When compared to traditional laparotomy, the use of laparoscopic techniques results in reduced trauma, shortened hospital stay, decreased pain, and reduced cosmetic disfigurement.

The trocars may be sized to provide ports of differing sizes, typically of about 5 mm to 11 mm diameter. The largest trocar port diameter is on the order of about 11 min. The actual incision diameter to provide a given sized port may be slightly smaller than the port, the surrounding flesh stretching somewhat to accommodate the slightly larger trocar port.

Surgical tools used in laparoscopic procedures must have cross-sections which will pass through these small diameter ports. Currently, such tools as retractors, forceps, graspers, suture needles, scissors, knives, laser incision instruments, specimen bags, etc. are available. Each of these laparoscopic tools requires a lengthy rigid handle portion which extends through the laparoscopic trocar port for external manipulation by the surgeon. The long span between the manipulated organ and an available trocar port often makes the desired objective difficult to achieve. While it may be theoretically advantageous to have a sufficient number of trocar ports so that long reaches are unnecessary, such a large number is generally impractical.

Because accessibility to the body cavity is limited by the numbers, placement and sizes of the trocars used, multiple surgical instruments must often be internally extended from remote trocar ports to the target area. Such manipulation over considerable distances complicates the surgical procedures, makes precise manipulation difficult, and crowds the surgical target area. In addition, the presence of intermediate body organs and vessels restricts the accessibility and use of prior art rigid laparoscopic tools at target areas distant from the trocar port.

While laparoscopic techniques significantly reduce the trauma associated with surgical operations, the number of laparoscopic ports in an operation is trauma-limited, nevertheless. In some situations, surgery requiring more than about 5 or 7 laparoscopic ports may be better performed by traditional laparotomic procedures.

The need exists for revised techniques and tools for reducing surgery-induced trauma in laparoscopic surgery.

BRIEF SUMMARY OF THE INVENTION

To avoid many of the difficulties generally associated with laparoscopic surgery, a modular two-part surgical tool system is disclosed which enables an instrument to be externally manipulated by a surgeon close to or adjacent the area where the instrument is to be used. The tool manipulation site is independent of the location of existing trocars, i.e. laparoscopic ports. The need for long tool handles which in conventional laparoscopic procedures must span the distance from the nearest trocar port to the target surgery area is avoided. The use of modular two-part laparoscopic tools of this invention enhances the advantages and broadens the applicability of laparoscopic surgical procedures when compared to traditional laparotomy.

The miniature tool system of this invention is a two-part modular, i.e. interchangeable laparoscopic surgical tool comprising an instrument shaft with a handle and an intracorporeally attachable/detachable head. The instrument head is dimensioned to be insertable through a laparoscopic port, i.e. a trocar port, into a body cavity such as the abdominal or chest cavity. The elongate shaft has a proximate end comprising a handle and an opposite distal end portion which is tapered to a sharp point. The point enables the shaft to pierce through the cavity wall to form a small "needle hole" which stretches to the size of the shaft diameter, i.e. about 1-8 min. In general, a shaft diameter of about 2 to 5 mm is used, but a greater or lesser diameter may be used depending upon the required rigidity and the particular type of operation. The distal, i.e. sharpened tapered end of the shaft is further configured for intracorporeal detachable attachment to the shank portion of an instrument head. Thus, following its further insertion through the "needle hole", the first end of the shaft is intracorporeally attached to the shank of the instrument head, the latter being manipulated by a standard laparoscopic insertion tool, e.g. forceps or grasper passing through a trocar port, to complete the joinder of the shaft to the instrument and form the two-part tool.

The two-part surgical tool may then be manipulated by controlling the handle portion passing through the "needle hole".

The small "needle hole" may be located at a site on the cavity wall for most efficient intracorporeal use of the tool, enabling more precise control over its use as compared to instruments manipulated from the end of a much longer handle passing through a distant trocar port. In addition, the small "needle hole" results in reduced trauma as compared to the use of additional laparoscopic, i.e. trocar ports, or conventional full-blown laparotomy.

Long distance tool manipulation of the prior art requires wider and heavier handles to achieve the required rigidity. In the present invention, tool manipulation at a shorter distance enables use of tool shafts which are narrower and lighter in weight, yet having improved control of the operative end.

A wide variety of instrument styles and functions is contemplated, satisfying the range of surgical instruments which may be found useful. Handles of varied length and diameter may interchangeably be affixed intracorporeally or extracorporeally with any of the instruments to adapt to each need. The instruments illustrated and described herein are exemplary of the wide range of possible instrument types.

The instrument heads as well as the multi-purpose shaft may be inexpensively manufactured for disposable use, if desired.

The features and advantages of the invention will be readily understood by reading the following description in conjunction with the accompanying figures of the drawings wherein like reference numerals have been applied to designate like elements throughout the several views.

DESCRIPTION OF THE PREFERRED EMBODIMENTS

Figure 1:
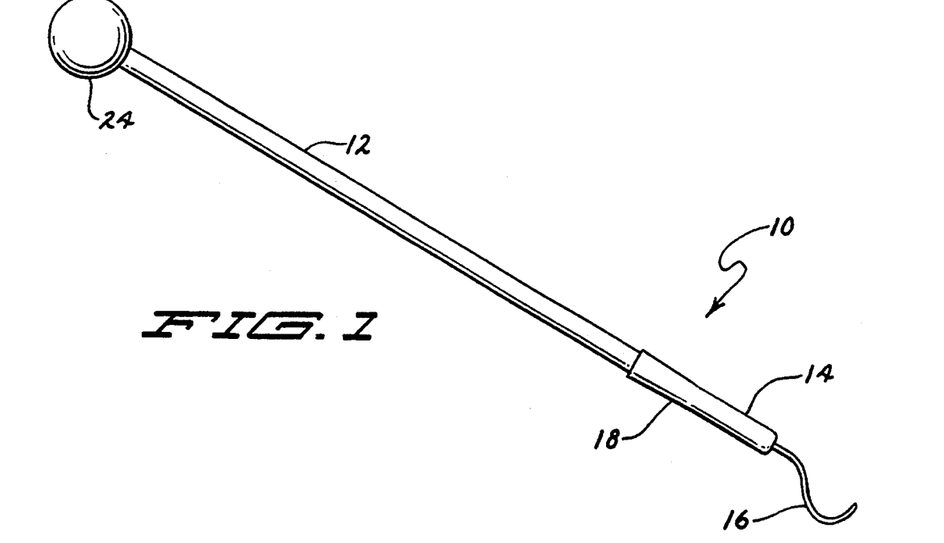
FIG. 1 is a lateral view of a modular two-part laparoscopic surgery tool of the invention.

With reference to the drawings, and particularly to FIG. 1, a two-part modular tool 10 of the present invention is shown fully assembled. The two parts as separately depicted in FIGS. 2-14 comprise an elongate shaft 12 and an instrument head 14 which includes an instrument 16 fixed to a hollow shank 18. In the "snap-on" embodiment of FIG. 3, the shaft 12 may be detachably attached to the instrument head 14 by insertion into the hollow shank 18 until the detent 20 (see FIG. 3) in the shank 18 snaps into a corresponding recess 22 in the shaft. The shank 18 is of a sufficiently resilient material so that the detent 20 may pass along the shaft 12 and coaxially into the recess 22 with hand applied pressure.

Figure 3:
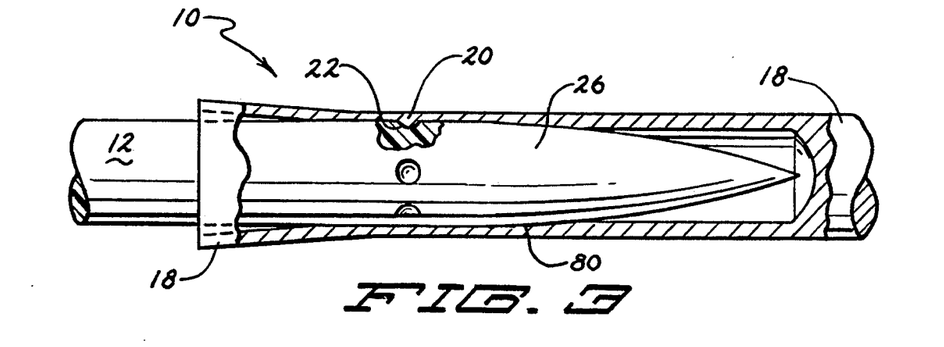
FIG. 3 is an enlarged partially cutaway lateral view of a shaft-instrument connection of an embodiment of the surgery tool of the invention.

Likewise, the shaft 12 and shank 18 may be parted by moderate hand tension. The tool 10 is configured for intracorporeal assembly and dissembly, that is, attachment and detachment within a closed body cavity from a location outside of the cavity. Preferably, a plurality of recesses 22 encircle the shaft 12 so that the shaft need not be rotated up to a full turn to align the recess 22 with the detent 20. Alternatively, a plurality of recesses 22 may be formed on the inside surface of the shank 18, or multiple detents 20 and recesses 22 may be used in combination. The figure shows multiple recesses 22 in shaft 12.

Figure 2:
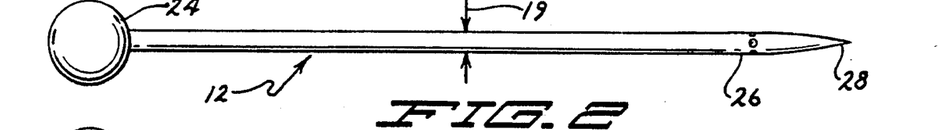
FIG. 2 is a lateral view of the shaft portion of an embodiment of the two-part surgery tool of the invention.

As shown in FIG. 2, the shaft 12 comprises an elongate acuminate member of narrow width 19, e.g. 1-8 mm and more typically 2-5 mm, and generally circular in cross section. It has a first or proximate end portion 24 which is a handle portion configured for manipulation by a member of the surgical team, and an opposite distal attachment end 26 which has several functions. Distal end 26 is tapered to a surgically sharp point 28. The sharp point 28 enables the shaft 12 to be driven through, i.e. to puncture a body wall such as an abdominal or chest wall, forming a relatively small "needle" hole 30 (see FIG. 13) into the body cavity. The handle portion 24 enables application of downward pressure onto the sharp point 28 for puncturing the body wall, forming a needle hole. The handle portion 24 also enables precise sealable manipulation of the instrument through a gas retaining laparoscopic port, and prevents the shaft 12 from slipping entirely through the needle hole into the body cavity. After the sharp point 28 has been driven through the body wall, the shaft 12 may be intracorporeally joined to the shank 18 of an instrument head 14 inserted through a trocar port, i.e. a laparoscopic port. The thin shaft 12 may be maintained in the needle hole 30 so that the instrument head 14 in the body cavity is controlled from exterior the needle hole 30 in the body wall. The wall structure seals the circumference of shaft 12 within the hole 30 to prevent leakage of insufflation gas therefrom.

Figure 4:
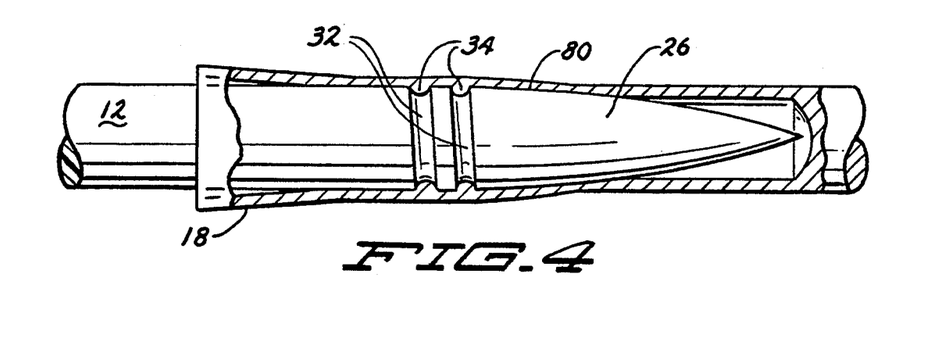
FIG. 4 is an enlarged partially cutaway lateral view of a shaft-instrument connection of another embodiment of the surgery tool of the invention.

Another embodiment of the attachment means is illustrated in FIG. 4. The tapered attachment portion 26 of shaft has an external threaded section 32 which matches an internal threaded section 34 of the hollow shank 18. The two are joined together by inserting the attachment portion 26 into the shank 18 and twisting to effectively lock the two parts together. The tool may be dissembled either intracorporeally or extracorporeally by unscrewing the shaft 12 from the shank 18.

The shaft-shank interface 80 is sized to require the shank 18 to be slightly expanded or distorted for joinder of shaft 12 to shank 18. However, portions of the shaft and shank interface 80 which lie forward of the detent 20 or threads 32, 34 are shown as being configured to produce a tight fit therebetween. Thus, when joined, there is no wobble in the tool 10.

The instrument heads 14 are sized to be passable through a trocar port by a laparoscopic grasper or forceps for intracorporeal joinder to a shaft 12. In some cases, it may be desirable to join the instrument head 14 and shaft 12 outside of the body cavity and pass the assembled tool 10 through the trocar port into the body cavity-for manipulation through the port.

Each of the exemplary instrument heads 14 shown in FIGS. 5 through 12 is shown with a hollow shank 18 into which the distal end portion 26 of the shaft 12 may be lockingly inserted. The shank 18 is shown with a flared open end 38 for ease of inserting the shaft 12.

Other attachment means, not shown, which permit intracorporeal detachable attachment may be used. Thus, a combination of screw threads with a stop may be used for preventing undesired rotation of the tool. Other attachment means, including other types of detents or a simple friction fit, may alternatively be used.

While the shaft 12 is shown as straight, it may also be arcuate or have reverse curvature for particular applications.

Figure 5:
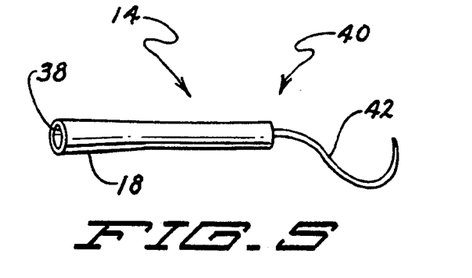
FIG. 5 is a generally lateral view of an instrument head of the invention comprising a laparoscopic hook retractor.

FIG. 5 shows a hook instrument 40 with a hook 42. The hook 42 may be used for retracting, for example, and may be formed of metal, plastic, or other suitable material.

Figure 6:
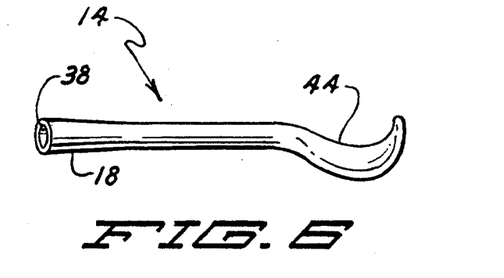
FIG. 6 is a generally lateral view of an instrument head of the invention comprising a laparoscopic curved retractor.

FIG. 6 illustrates a curved retraction instrument 44 for pushing or pulling body members intracorporeally. It may be formed of plastic, metal, or other suitable material.

Figure 7:
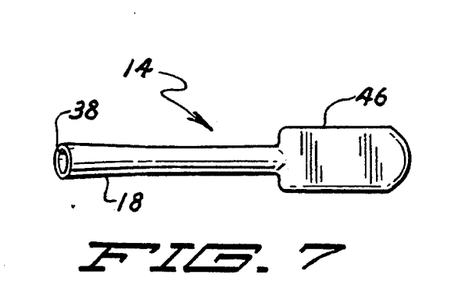
FIG. 7 is a generally lateral view of an instrument head of the invention including a laparoscopic fiat retractor.

FIG. 7 shows a flat retractor 46 for holding or pushing body members. The instrument has at least one generally flat side, and may be formed of i.e. plastic, metal or other suitable material.

Figure 8:
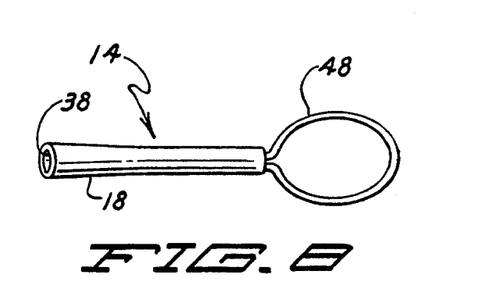
FIG. 8 is a generally lateral view of an instrument head of the invention including a laparoscopic ring retraction instrument.

FIG. 8 shows a ring retractor instrument 48 for pushing or pulling body organs. The ring instrument may be formed of metal, strong plastic or other suitable material.

Figure 9:
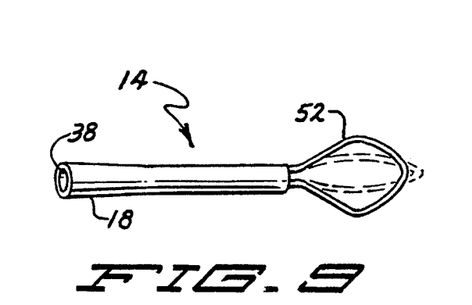
FIG. 9 is a generally lateral view of an instrument head of the invention including a laparoscopic flexible ring instrument.

FIG. 9 shows a flexible ring type instrument 52 useful for retraction. The flexible ring may be compressed for passage through a laparoscopic port, and may have an open diameter considerably larger than the port diameter. The flexible ring is preferably made of a pliant material such as spring metal, pliant plastic or other suitable flexible material.

Figure 10:
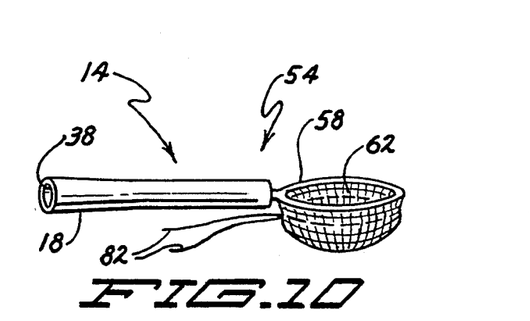
FIG. 10 is a generally lateral view of an instrument head of the invention including a laparoscopic basket instrument.
Figure 11:
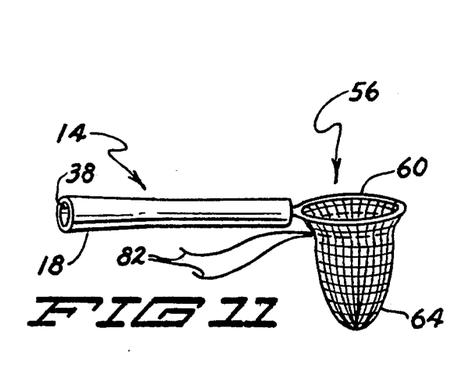
FIG. 11 is a generally lateral view of an instrument head of the invention including a laparoscopic bag instrument.

FIGS. 10 and 11 illustrate a basket type instrument 54 and a bag type instrument 56, respectively. These collection type instruments have rims 58, 60 which may be formed of metal, plastic, or other suitable material, and the basket 62 and bag 64 may be formed of any material formable as a mesh. The basket 62 and bag 64 are shown with drawstrings 82 by which the upper portion of the basket and bag may be drawn to a closed position, locking objects therein. These types of instruments are particularly useful for removing dissected body parts from the body cavity through a laparoscopic port.

Figure 12:
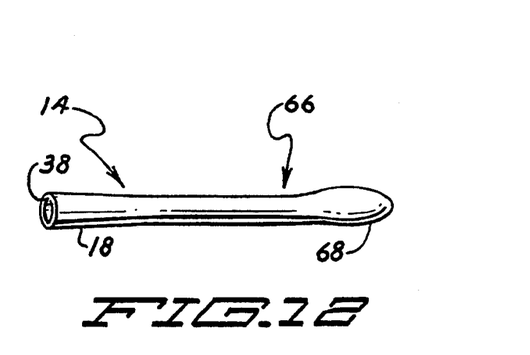
FIG. 12 is a generally lateral view of a laparoscopic round dissector/pusher of the invention.

FIG. 12 depicts a round dissector/pusher 66. An edge portion 68 may be sharpened for cutting. The instrument is preferably formed of metal or plastic.

Figure 13:
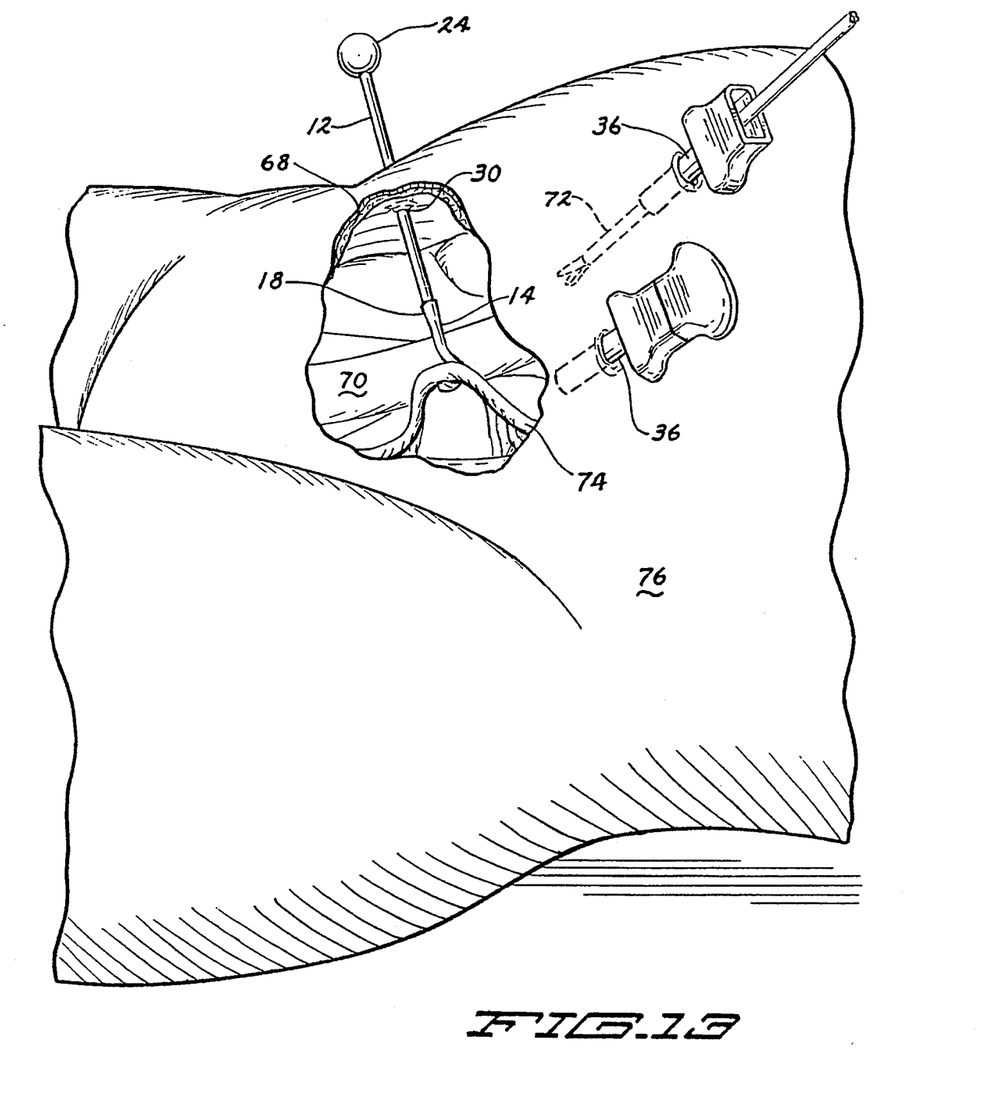
FIG. 13 is a partially cut-away left antero/lateral view of the abdominal cavity of a human body illustrating the installation and use of a modular two-part laparoscopic surgery tool of the invention.

FIG. 13 illustrates general methods for using the tools of this invention. A surgical procedure is shown in the abdominal cavity 70 of torso 76 to include the placement of two trocar ports 36 through the abdominal cavity wall 68 and insufflation of the body cavity.

In the procedure, the instrument head 14 is passed through an existing laparoscopic port 36, typically of 10-11 mm diameter and less than about 12-15 mm, into the body cavity 70 using a forceps, grasper or other insertion tool 72. The tool 72 may be withdrawn or used for other purposes once the head 14 and shaft 12 are intracorporeally joined in the cavity.

Figure 14:
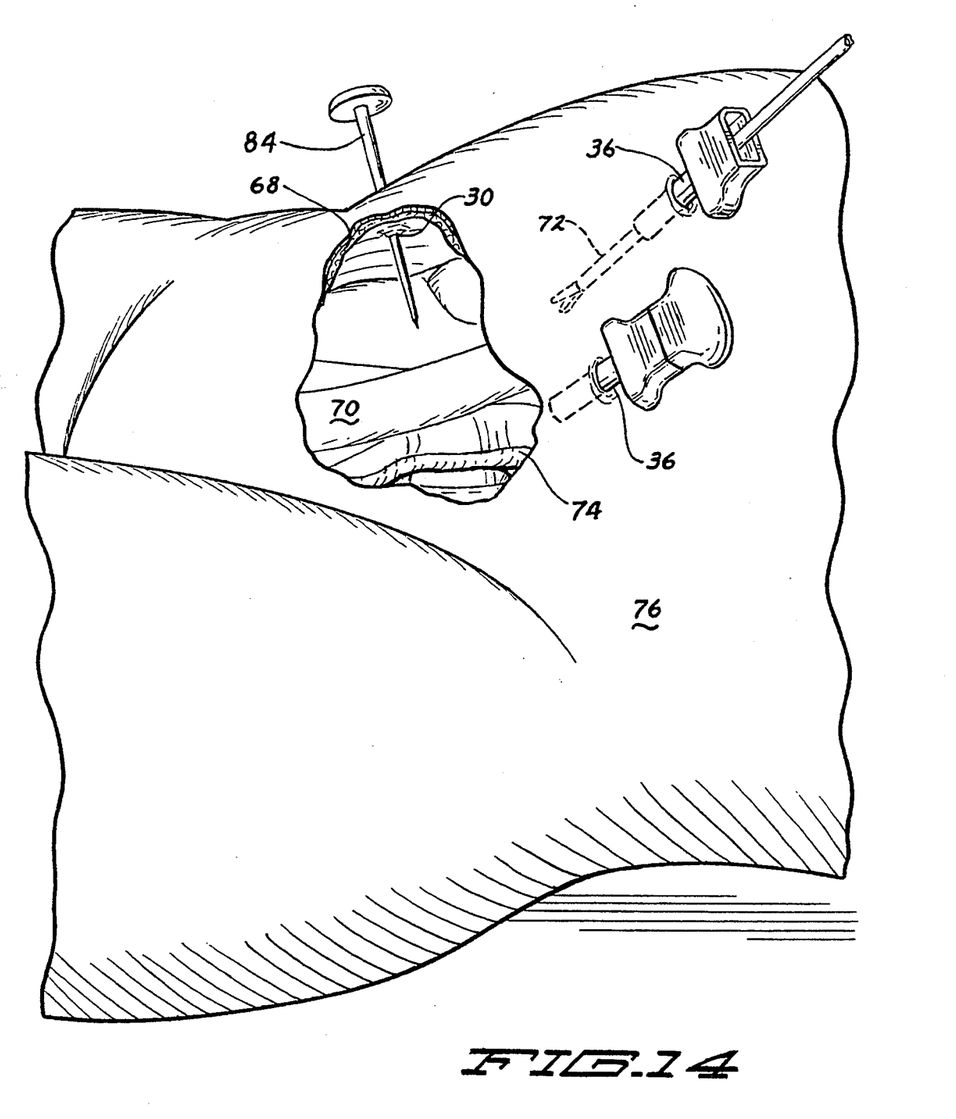
FIG. 14 is a partially cut-away left antero/lateral view of a human body illustrating the punctuating of the body wall by a needle tool.

A needle hole 30 is made through the cavity wall 68 by the sharp point 28 of the thin acuminate shaft 12 or by another tool e.g. a needle 84 the alternative step of puncturing the cavity wall 68 to from needle hole 30 with a separate tool such as needle 84 is illustrated in FIG. 14. The needle hole 30 is formed at a location which enables the two-part tool 10 to be efficiently operated. The tapered end 26 is then inserted into the cavity 70 and further inserted and locked in the hollow shank 18 of exemplary instrument head 14. During this step, the instrument head 14 is maintained in place by a grasper or forceps 72. The two-part tool is shown being manually manipulated from outside of the cavity 70 to retract a vessel 74. In this example, a curved instrument head such as shown in FIG. 6 is being used. The system is operable with any type of instrument having a shank which connects to a thin shaft and is passable through a trocar port.

It is anticipated that various changes and modifications may be made in the materials and methods of construction, arrangement, and method of operation of the tools disclosed herein without departing from the spirit and scope of the invention as defined in the following claims.

What is claimed is:

1. A two-art modular laparoscopic tool for use with laparoscopic surgical procedures in a body cavity, comprising:
   an instrument head comprising:
      an instrument passable through a laparoscopic port; and
      an elongate shank attached to said instrument; and
   an elongate shaft having a tapered end portion with first detachable attachment means for detachable attachment to said shank and an opposite handle portion, said tapered end portion insertable through a needle hole into said body cavity for intracorporeal detachable attachment to a second detachable attachment means in said shank for detachable attachment to said shaft;
   wherein said tapered end portion comprises a sharp cutting point for puncture and passage through a body wall.

2. The two-part tool of claim 1, wherein said shank is rigidly fixed to the instrument.

3. The two-part tool of claim 1, wherein said shank is hollow and said tapered end portion of said shaft is removably insertable into said shank.

4. The two-part tool of claim 3, wherein said shank is coaxial with said shank, and said second detachable attachment means comprises a detent on the inside surface of the hollow shank which latches in said first attachment means comprising a corresponding recess in said shaft, said shaft attachable to said shank by coaxial compression between said shaft and said shank for attachment thereto, said shaft detachable from said shank by application of coaxial tension therebetween.

5. The two-part tool of claim 3, wherein said shank is formed of thin resilient material.

6. The two-part tool of claim 3, wherein said second detachable attachment means comprises internal screw threads within said shank and said first detachable attachment means comprises matching external screw threads on said shaft.

7. The two-part tool of claim 1, wherein the instrument head is passable through a port diameter less than about 12-15 mm.

8. The two-part tool of claim 1, wherein said instrument comprises one of a retractor, dissector and collection device.

9. The two-part tool of claim 1, wherein said instrument comprises a flexible open-ended basket or bag mounted on an open rim and having means for closing the open end to entrap objects therein.

10. The two-part tool of claim 1, wherein said shaft has a generally circular cross-section for sealable manipulation through a gas retaining laparoscopic port.

11. The two-part tool of claim 10, wherein said handle portion has a diameter of 1~8 mm.

12. The two-part tool of claim 10, wherein said handle portion has a diameter of 2~5 mm.

13. The two-part tool of claim 1, wherein said instrument head includes a flexible material shaped into a basket or bag shape for holding objects and compressible for passage through said laparoscopic port.

14. A multi-purpose instrument useful in laparoscopic surgery, comprising:
   an elongate narrow shaft having a first tapered end culminating in a sharp point for surgically puncturing a body wall for forming needle hole, a second enlarged end comprising a handle for manipulation of said multi-purpose instrument through said needle hole, and first locking means on said first tapered end; and
   a laparoscopic surgical instrument head having a shank with a hollow interior with a second locking means therein,;
   wherein said first locking means is detachably attachable to said second locking means.

15. The multi-purpose instrument of claim 14, wherein said first locking means comprises a recess on the first tapered end of said shaft, and said corresponding second locking means comprises a detent in the hollow interior of said shank, said detent and recess configured to detachably engage for locking said shaft to said shank.

16. The multi-purpose instrument of claim 14, wherein said first and second locking means comprise matching screw threads on said first tapered end of said shaft and said hollow interior of said shank.

17. The multi-purpose instrument of claim 14, wherein the diameter of said elongate shaft is 1–8 mm.

18. A laparoscopic method for performing surgical procedures in a body cavity, comprising:
   establishing a laparoscopic trocar port across a body wall into a body cavity;
   introducing a miniature instrument having a shank joined thereto thrown said port into said body cavity with a laparoscopic insertion tool;
   puncturing said body wall with a needle to form a needle hole and inserting therethrough a thin acuminate shaft having one end configured to attach to said shank;
   intracorporeally joining said shaft to said shank while manipulating said instrument through said port; and
   detaching said insertion tool from said instrument for manipulation by said shaft passing through said needle hole.

19. The method of claim 18, further comprising the step of insufflating said cavity.

20. The method of claim 18, comprising the further steps of:
   grasping said instrument with the insertion tool passing through said laparoscopic port;
   detaching said shaft from said shank; and
   recovering said instrument through said laparoscopic port.

21. A laparoscopic method for performing surgical procedures in a body cavity, comprising:
   establishing a laparoscopic trocar port across a body wall into a body cavity;
   introducing a miniature instrument having a shank joined thereto through said port into said body cavity with a laparoscopic insertion tool;
   puncturing said body wall with a sharpened end of a thin acuminate shaft to form a needle hole and inserting therethrough said shaft having said sharpened end configured to be attached to said shank;
   intracorporeally joining said sharpened end of said shank while manipulating said instrument through said port; and
   detaching said insertion tool from said instrument for manipulation by said shaft passing through said needle hole.

22. The method of claim 21, further comprising the step of insufflating said cavity.

23. The method of claim 21, comprising the further steps of:
   grasping said instrument with the insertion tool passing through said laparoscopic port;
   detaching said shaft from said shank; and
   recovering said instrument through said laparoscopic port.

* * * * *

UNITED STATES PATENT AND TRADEMARK OFFICE
CERTIFICATE OF CORRECTION

PATENT NO. : 5,352,219
DATED : Oct. 4, 1994
INVENTOR(S) : Pratap K. Reddy

It is certified that error appears in the above-indentified patent and that said Letters Patent is hereby corrected as shown below:

Col. 1, line 16, delete "carded" and insert --carried-- therefor.

Col. 1, line 29, delete "min." and substitute --mm.-- therefor.

Col. 3, line 30, delete "fiat" and insert --flat-- therefor.

Col. 3, line 51, delete "punctuating" and insert --puncturing-- therefor.

Col. 3, line 59, delete "2-14" and insert --2-4-- therefor.

Col. 5, line 61, immediately following "84" insert a --.--.

Col. 5, line 61, before "alternative" delete "the" and substitute --The-- therefor.

IN THE CLAIMS:

Claim 1, col. 6, line 16, delete "two-art" and insert --two-part-- therefor.

Claim 4, col. 6, line 40, delete "shank" and substitute --shaft-- therefor.

Claim 11, col. 7, line 2, delete "1-8" and insert --1-8-- therefor.

Claim 12, col. 7, line 4, delete "2-5" and insert --2-5--

UNITED STATES PATENT AND TRADEMARK OFFICE
CERTIFICATE OF CORRECTION

PATENT NO. : 5,352,219
DATED : Oct. 4, 1994
INVENTOR(S) : Pratap K. Reddy

It is certified that error appears in the above-indentified patent and that said Letters Patent is hereby corrected as shown below:

therefor.

Claim 18, col. 7, line 41, delete "thrown" and insert --through-- therefor.

Signed and Sealed this

Twenty-sixth Day of September, 1995

Attest:

BRUCE LEHMAN

Attesting Officer

Commissioner of Patents and Trademarks